United States Patent
Millerd

(10) Patent No.: US 8,403,893 B2
(45) Date of Patent: Mar. 26, 2013

(54) PRE-FILLED CARTRIDGE PLUNGER METHOD

(75) Inventor: Don Millerd, San Diego, CA (US)

(73) Assignee: MedPro Safety Products, Inc., Lexington, KY (US)

( * ) Notice: Subject to any disclaimer, the term of this patent is extended or adjusted under 35 U.S.C. 154(b) by 0 days.

(21) Appl. No.: 12/821,707

(22) Filed: Jun. 23, 2010

(65) Prior Publication Data

US 2010/0262121 A1   Oct. 14, 2010

Related U.S. Application Data

(63) Continuation of application No. 12/256,139, filed on Oct. 22, 2008, now Pat. No. 8,157,771, which is a continuation of application No. 11/211,336, filed on Aug. 25, 2005, now abandoned.

(51) Int. Cl.
   *A61M 5/32* (2006.01)

(52) U.S. Cl. .......................... 604/198; 604/192; 604/110

(58) Field of Classification Search .................. 604/110, 604/192, 195, 197, 198, 201, 203, 232
   See application file for complete search history.

(56) References Cited

U.S. PATENT DOCUMENTS

| | | | |
|---|---|---|---|
| 3,941,131 A * | 3/1976 | Ogle | ............................ 604/203 |
| 4,813,940 A | 3/1989 | Parry | |
| 4,911,693 A | 3/1990 | Paris | |
| 5,061,251 A | 10/1991 | Juhasz | |
| 5,104,384 A | 4/1992 | Parry | |
| 5,167,640 A | 12/1992 | Balding | |
| 5,197,953 A | 3/1993 | Colonna | |
| 5,242,420 A | 9/1993 | Martin | |
| 5,267,972 A | 12/1993 | Anderson | |
| 5,292,314 A | 3/1994 | D'Alessio et al. | |
| 5,376,080 A | 12/1994 | Petrussa | |
| 5,389,085 A | 2/1995 | D'Alessio et al. | |
| 5,549,558 A | 8/1996 | Martin | |
| 5,688,241 A | 11/1997 | Asbaghi | |
| 5,976,111 A | 11/1999 | Hart | |
| 6,030,366 A | 2/2000 | Mitchell | |
| 6,224,576 B1 | 5/2001 | Thorne et al. | |
| 6,379,336 B1 | 4/2002 | Asbaghi et al. | |
| 6,565,540 B1 * | 5/2003 | Perouse et al. | ................. 604/192 |
| 6,616,637 B2 * | 9/2003 | Alexander et al. | ............ 604/192 |
| 6,648,858 B2 | 11/2003 | Asbaghi | |
| 6,869,415 B2 * | 3/2005 | Asbaghi | ......................... 604/110 |
| 6,884,237 B2 | 4/2005 | Asbaghi | |
| 7,004,929 B2 | 2/2006 | McWethy et al. | |
| 2003/0187401 A1 | 10/2003 | Doyle | |

OTHER PUBLICATIONS

International Search Report dated Aug. 17, 2007 for Application No. PCT/US2006/11714.

* cited by examiner

*Primary Examiner* — Kevin C Sirmons
*Assistant Examiner* — Laura Schell
(74) *Attorney, Agent, or Firm* — Ulmer & Berne LLP

(57) ABSTRACT

A method involving a syringe, a pre-filled cartridge, a needle, a guard, and a release mechanism is described. The method may involve inserting the cartridge into the syringe. In some versions, the method may involve releasing the guard to cover a portion of the needle. In some versions, the method may involve the release retaining the guard in a retracted position. In some versions, the release may be operable to be actuated to release the guard. In some versions, the guard may be extended and locked once extended to cover the needle.

20 Claims, 3 Drawing Sheets

PRE-FILLED CARTRIDGE PLUNGER METHOD

PRIORITY

This application claims priority to U.S. Nonprovisional patent application Ser. No. 12/256,139, filed Oct. 22, 2008, entitled "Syringe Guard for Pre-Filled Medicament Vial", now U.S. Pat. No. 8,157,771, and U.S. Nonprovisional patent application Ser. No. 11/211,336, filed Aug. 25, 2005, entitled "Syringe Guard for Pre-Filled Medicament Vial,", now abandoned, the disclosures of which are herein incorporated by reference in their entirety.

FIELD OF THE INVENTION

The present invention pertains generally to fluid infusion devices. More particularly, the present invention pertains to fluid infusion devices that include an automatically activated guard for covering and protecting the needle of the device after its use. The present invention is particularly, but not exclusively, useful as a syringe, with a needle guard, where the syringe is engageable with a pre-filled fluid vial to establish a fluid infusion device.

BACKGROUND OF THE INVENTION

Fluid medicaments, as well as other commercially available fluids, can be purchased in a variety of different type containers. The container of particular interest here, however, is the pre-filled vial. Typically, such a container/vial is made of glass, and is formed as a hollow cylindrical tube that has two open ends. One end can then be closed with a plug, and a stopper can be inserted through the opposite end to create a fluid chamber in the vial between the plug and the stopper. Thus, the chamber of the container/vial can then be filled with a predetermined amount of a desired fluid (e.g. a fluid medicament).

For the context wherein a container, such as the pre-filled fluid vial described above, is to be used for an infusion of fluid, the fluid must somehow be brought into fluid communication with a needle. Heretofore, a typical procedure for accomplishing this purpose has been to penetrate the stopper of the container/vial with a hypodermic needle. Fluid in the vial is then evacuated from the fluid chamber of the vial. In this example, the fluid is caused to flow through the needle and into the fluid chamber of a syringe. The now-filled syringe can then be disengaged from the vial and used for an infusion. The procedure just described, however, is somewhat cumbersome. In particular, this is so because the filling of the syringe, and the infusion of the fluid are performed as two separate and distinct operations. And, as such, each has its own attendant hazards. Further, with the increased awareness of communicable diseases (e.g. AIDS), the protection of the user from unwanted needle sticks has become of paramount importance. The consequence here is that the commercial potential for using pre-filled fluid vials may be enhanced by reducing the number of required manipulations in a procedure, and by directly incorporating pre-filled fluid vials into systems/devices that automatically protect the user from unwanted or inadvertent needle sticks.

In light of the above, it is an object of the present invention to provide a device which can be engaged with a pre-filled fluid vial for infusing fluid directly from the vial. Another object of the present invention is to provide a device for infusing a fluid medicament that automatically protects the user from unwanted or inadvertent needle sticks after the fluid from a pre-filled fluid vial has been infused. Yet another object of the present invention is to provide a device for infusing fluid from a pre-filled vial that is easy to use, is relatively simple to manufacture, and is comparatively cost effective.

SUMMARY OF THE INVENTION

In accordance with the present invention, a device is provided for expelling fluid from a pre-filled vial, through a needle. As envisioned for the present invention, the pre-filled fluid vial will have a hollow, cylindrical-shaped, glass wall, with a plug covering one of its open ends. A stopper will be inserted into the other open end of the cylindrical wall to thereby create a fluid chamber in the vial for holding fluid therein between the plug and the stopper.

Structurally, the device of the present invention includes a hollow, cylindrical-shaped syringe body that is formed with a lumen and has an open proximal end, and an open distal end. Thus, the syringe body defines a longitudinal axis that extends between the two ends. Further, an elongated adapter is axially aligned within the syringe body, and it is fixedly mounted in the lumen of the syringe body. As so mounted, a space is created between the adapter and the syringe body.

For the device of the present invention, the adapter is substantially cylindrical in shape, and it is formed with a lumen. Additionally, a hollow needle is mounted in the lumen of the adapter such that the needle extends along the longitudinal axis of the syringe body. Importantly, the adapter is formed with both a proximal hinge, and a distal hinge. Both of these hinges are so-called "living" hinges, and they are longitudinally aligned with each other. The adapter is also formed with at least one slot that extends along its length.

In addition to the needle, a guard is also mounted in the lumen of the adapter. Specifically, the guard is cylindrical shaped and it is positioned within the lumen of the adapter for axial movement over the needle between a first position and a second position. In its first position, the guard is held within the syringe body to expose a distal portion of the needle as it extends beyond the distal end of the syringe body. Structurally, the guard is held in the first position by a flexible hinge lock on the guard that engages with the adapter. Upon release of the hinge lock, however, the guard moves distally into its second position. In its second position, the guard extends beyond the distal end of the syringe body, to cover the distal portion of the needle. For the device of the present invention, this distal movement of the guard in the axial direction is caused by a spring that is located between the adapter and the guard to push distally against the guard. This movement, however, is limited by a tab on the guard that extends into the slot of the adapter.

In operation, the fluid vial is first engaged with the proximal end of the syringe body. With this engagement, the proximal end of the needle pierces the stopper in the vial. This then establishes fluid communication between the fluid chamber of the vial and the needle. Also, during this engagement, the wall of the vial is introduced into the space between the syringe body and the adapter. Subsequently, as the wall of the vial is advanced distally into the space between the syringe body and the adapter, it activates the proximal hinge of the adapter. When activated, the proximal hinge of the adapter releases the hinge lock of the guard for movement of the guard in the distal direction. As indicated above, this causes the guard to extend beyond the distal end of the syringe body to cover and protect the distal end of the needle. It is to be noted here, however, that if the needle is being used for an infusion, the body into which the infusion is being made may prevent the guard from making its full distal movement. Next, as further distal movement of the wall of the vial is made during the infusion, the wall repositions the distal hinge of the adapter to prevent a subsequent proximal movement of the guard. Thus, subsequent to an infusion, and after the needle has been withdrawn from the body being infused, the guard remains extended beyond the distal end of the syringe body. This causes the guard to cover the needle and to thereby protect against accidental of inadvertent sticks by the needle.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
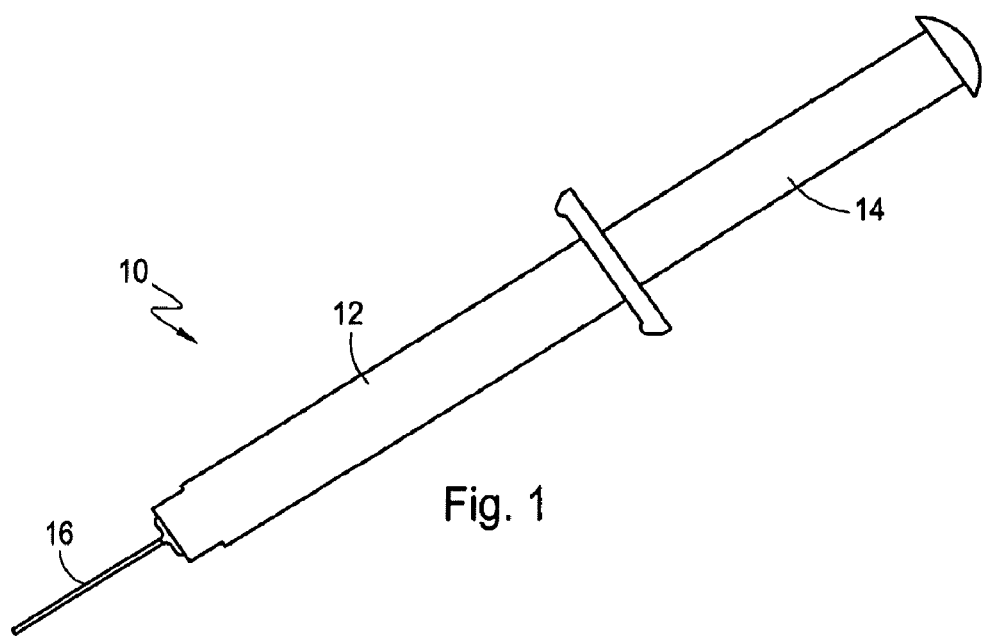
FIG. 1 is a view of an assembled device for infusing fluids from a pre-filled vial, in accordance with the present invention.

Referring initially to FIG. 1, a device for expelling fluid from a pre-filled vial is shown and is generally designated 10. As shown, the device 10 includes a syringe body 12 that is engaged with a pre-filled vial/container 14. In accordance with the discussion below, it will be appreciated that the device 10 is useful for expelling fluid from the vial 14, and through a hollow needle 16, during an infusion procedure. Further, it will also be appreciated that the device 10 provides structure for covering the needle 16 after the infusion procedure has been completed. The purpose here is to prevent accidental or inadvertent sticks with the needle 16 that might otherwise occur after using the device 10. Preferably, the needle 16 is made of a stainless steel type material.

Figure 3:
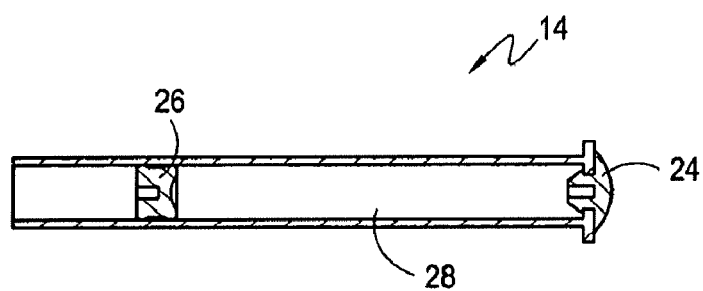
FIG. 3 is a cross section view of a pre-filled vial for use with the device of the present invention as seen along the line 3-3 in FIG. 1.
Figure 2:
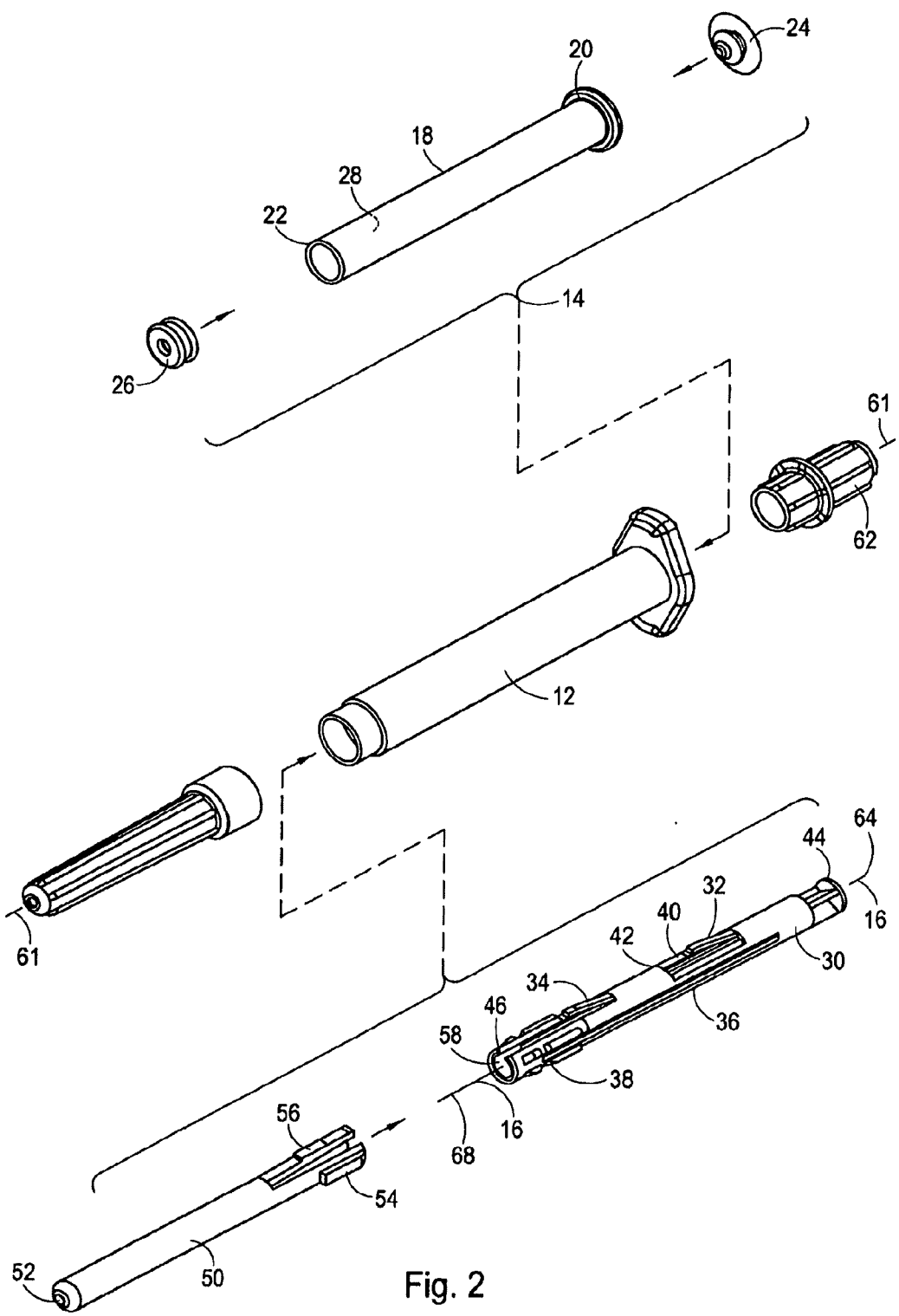
FIG. 2 is an exploded perspective view of the component elements of the device.

The various structural components of the device 10 will, perhaps, be best appreciated with reference to FIG. 2. There it can be seen that the pre-filled vial 14 includes a hollow cylindrical wall 18 that has both an open proximal end 20 and an open distal end 22. Further, the vial 14 includes a plug 24 and a stopper 26. When the vial 14 is assembled, as shown in FIG. 3, the plug 24 is positioned to cover the proximal end 20, and the stopper 26 is inserted through the distal end 22. Thus, a fluid chamber 28 is created for the vial 14. A fluid (e.g. a fluid medicament) can then be held inside the fluid chamber 28 that is surrounded by the wall 18 and enclosed by the plug 24 and the stopper 26. As intended for the device 10, the stopper 26 is moveable within the vial 14, and the wall 18 is preferably made of a rigid transparent material, such as glass.

Still referring to FIG. 2, it will be seen that the device 10 includes an adapter 30. As shown, the adapter 30 is elongated and is substantially cylindrical in shape. It is also shown in FIG. 2 that the adapter 30 is formed with a proximal hinge 32 and a distal hinge 34. For purposes of the present invention, both of the hinges 32 and 34 are so-called "living" hinges, in that they are integral with the adapter 30. It is also seen in FIG. 2 that the adapter 30 is formed with a slot 36 that extends longitudinally along the adapter 30. Actually, the adapter 30 can have two such slots that are diametrically opposite each other (one such slot, however, is not shown in FIG. 2). Further, the adapter 30 is formed with a series of circumferentially oriented structural detents 38. Also, in conjunction with the proximal hinge 32, the adapter 30 is formed with a slit 40 into which the hinge 32 can be deflected. As shown, the slit 40 creates an abutment 42 at its distal end.

Figure 4:
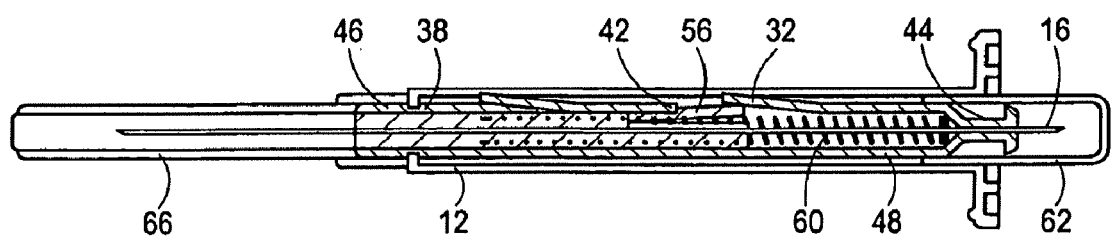
FIG. 4 is an elevation view of the device of the present invention ready for use with a pre-filled vial, and with portions broken away for clarity.

To best appreciate how the needle 16 and the adapter 30 are mounted on the syringe body 12, it is necessary to cross reference FIG. 2 with FIG. 4. With this cross-reference, it can be seen that the needle 16 is fixedly held at the proximal end 44 of the adapter 30 (see FIG. 4). Also, it can be seen that the detents 38 at the distal end 46 of the adapter 30 are fixedly engaged with the syringe body 12 (see FIG. 2). A consequence of this arrangement is that a space 48 is created between the adapter 30 and the syringe body 12.

FIG. 2 also shows that the device 10 includes a guard 50. Specifically, the guard 50 is a hollow, substantially cylindrical-shaped structure that defines a lumen 52, and that has diametrically opposed tabs 54 (one such tab 54 is not shown). Additionally, and importantly, the guard 50 is formed with a hinge lock 56. In its cooperation with the adapter 30, the guard 50 is inserted into the lumen 58 of the adapter 30, over the needle 16. More specifically, the guard 50 inserted into the lumen 58 until the hinge lock 56 of guard 50 extends through the slit 40 of adapter 30, for engagement of the hinge lock 56 with the abutment 42. In this combination, a spring 60 (see FIG. 4) is positioned between the guard 50 and the proximal end 44 of the adapter 30 to urge the guard 50 in a distal direction. This, of course, also urges the hinge lock 56 against the abutment 42 to hold the guard 50 in the position shown in FIG. 4.

With the guard 50 engaged to the adapter 30 as described above, and with the adapter 30 mounted on the syringe body 12 as also described above, the needle 16 will be longitudinally aligned along the axis 61 that is defined by the syringe body 12 (see FIG. 2). A proximal shield 62 can then be engaged with the syringe body 12 to cover and protect the proximal end 64 of the needle 16. Similarly, a distal shield 66 can be engaged with the syringe body 12 to cover and protect the distal end 68 of the needle 16. The result is a combination of components as shown in FIG. 4.

Figure 5A:
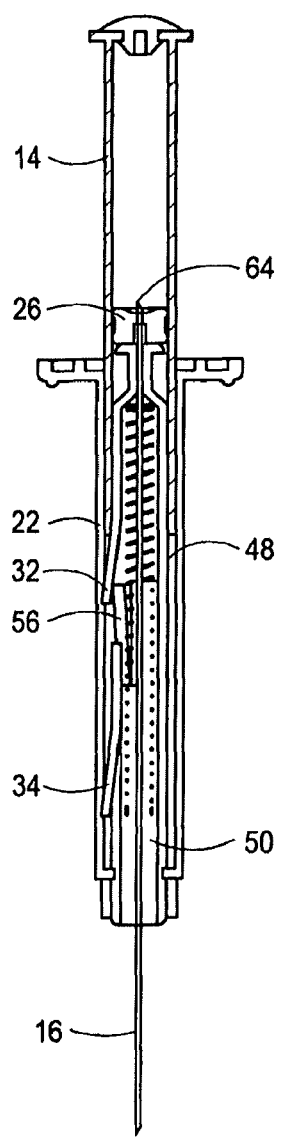
FIG. 5A is an elevation view of a device in accordance with the present invention when it is engaged with a pre-filled vial and ready for use in an infusion procedure, again, with portions of the device broken away for clarity.

In the operation of the device 10 of the present invention, the proximal shield 62 is removed from the syringe body 12 to expose the proximal end 64 of the needle 16. The pre-filled vial 14 is then engaged with the syringe body 12. Specifically, with this engagement, the proximal end 64 of the needle 16 penetrates through the stopper 26 to establish fluid communication between the needle 16 and fluid in the chamber 28 of vial 14. Also, with this engagement, the end 22 of wall 18 of the vial 14 is positioned in the space 48 between the syringe body 12 and the adapter 30. The distal shield 66 can then be removed from the syringe body 12 to expose a distal portion of the needle 16, as shown in FIG. 5A. The device 10 is now ready for an infusion procedure.

To perform an infusion procedure, with the device 10 in the configuration shown in FIG. 5A, the distal end 68 of the needle 16 is penetrated into the body that is to be infused (not shown). The pre-filled fluid vial 14 is then advanced distally along the axis 61, and into the syringe body 12. With this advancement, the end 22 of wall 18 comes into contact with the proximal hinge 32 of adapter 30 (see FIG. 5B). This contact then causes the proximal hinge 32 to deflect into the slit 40 of the adapter 30, and against the hinge lock 56 of the guard 50. In turn, this deflection moves the hinge lock 56 from its position against the abutment 42 of adapter 30. This frees the guard 50 for distal movement along the axis 61 under the influence of spring 60. As stated above, a full distal movement of the guard 50 may not occur at this time due to contact between the guard 50 and the body (not shown) into which the needle 16 may be penetrated.

Figure 5B:
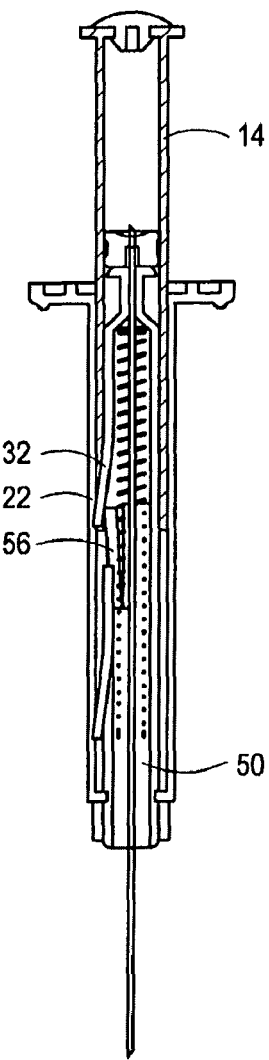
FIG. 5B is a view of the device shown in FIG. 5A during an infusion procedure, when configured with the vial engaging the adapter of the device to release the guard of the device for its distal movement.
Figure 5C:
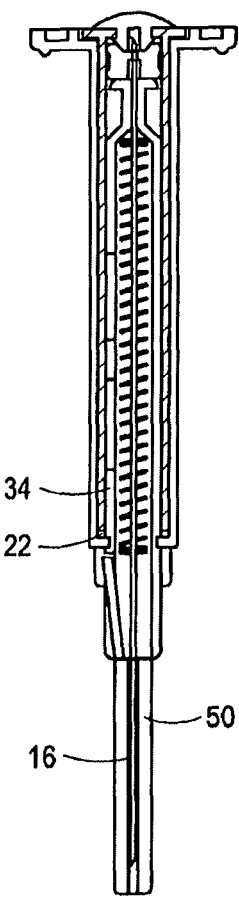
FIG. 5C is a view of the device shown in FIGS. 5A and 5B, after an infusion procedure.

As the pre-filled vial 14 is further advanced from its position in FIG. 5B to the position shown in FIG. 5C, the end 22 of wall 18 comes into contact with the distal hinge 34 of the adapter 30. This contact then causes the distal hinge 34 to be deflected and held in a position wherein it, the hinge 34, will block any return movement of the guard 50 in a proximal direction. Consequently, when the device 10 is configured as shown in FIG. 5C, and the guard 50 is no longer constrained to move distally, the hinge 34 and syringe body 12 cooperate to block a proximal movement of the guard 50. This causes the guard 50 to remain in place over the distal end 68 of the needle 16, to thereby prevent accidental or inadvertent "sticks".

While the particular Syringe Guard for Pre-Filled Medicament Vial as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A method comprising the steps of:
    providing a syringe comprising:
        (a) a syringe body, the syringe body having a central axis, a distal end, a proximal opening, and a lumen extending therethrough;
        (b) a needle in communication with the syringe body;
        (c) a pre-filled cartridge operable to be inserted into the proximal opening of the syringe body; and
        (d) a guard in communication with the syringe body, wherein the guard is configured to translate along the central axis of the syringe body; and
        (e) a distally projecting release, the distally projecting release having a free distal end and a fixed proximal end, wherein the distally projecting release is configured to release the guard from a retracted position to an extended position upon actuation;
    inserting the pre-filled cartridge into the proximal opening of the syringe body;
    establishing fluid communication between the needle and the pre-filled cartridge;
    releasing the guard from the retracted position to the extended position by depressing the distally projecting release radially inward; and
    urging the pre-filled cartridge distally, wherein distally actuating the pre-filled cartridge urges a fluid retained within the pre-filled cartridge through the needle.

2. The method of claim 1, wherein the pre-filled cartridge further comprises a distal bung, wherein the bung is configured to move proximally within the pre-filled cartridge as the pre-filled cartridge is urged distally within the syringe body.

3. The method of claim 1, wherein the guard is configured to translate within the syringe body.

4. The method of claim 1, wherein the fluid is a medicament.

5. The method of claim 1, wherein the step of urging the pre-filled cartridge distally further comprises actuating the distally projecting passive release mechanism such that the guard is permitted to move from the retracted position to the extended position.

6. The method of claim 1, wherein the pre-filled cartridge is a plunger operable to expel the fluid from the pre-filled cartridge in cooperation with the syringe body.

7. The method of claim 1, wherein the guard is locked in the extended position.

8. A method comprising the steps of:
    providing a syringe comprising:
        (a) a syringe body having a proximal end and a distal end;
        (b) a pre-filled cartridge, the pre-filled cartridge having a proximal end and a distal end, wherein a moveable stopper is positioned at the distal end of the pre-filled cartridge and a fixed stopper is positioned at the proximal end of the pre-filled cartridge;
        (c) a needle in communication with the syringe body, wherein the needle is configured to pierce the moveable stopper of the pre-filled cartridge to expel a fluid from the pre-filled cartridge;
        (d) a guard, the guard being configured to cover a distal end of the needle to prevent accidental needlesticks; and
        (e) a distally projecting release, the distally projecting release having a free distal end and a fixed proximal end, wherein the distally projecting release is configured to release the guard upon actuation;
    inserting the pre-filled cartridge into the proximal end of the syringe body;
    engaging a proximal end of the needle with the moveable stopper;
    advancing the pre-filled cartridge within the syringe body;
    advancing the moveable stopper proximally within the pre-filled cartridge such that a fluid retained within the pre-filled cartridge is expelled through the needle; and
    releasing the guard by depressing the distally projecting release radially inward such that the guard covers the distal end of the needle to prevent accidental needlesticks.

9. The method of claim 8, wherein the step of releasing the guard comprises releasing the guard by advancing the pre-filled cartridge to depress the distally projecting release.

10. The method of claim 8, wherein the step of releasing the guard comprises advancing the distal end of the pre-filled cartridge distally such that the distal end of the pre-filled cartridge is adjacent the distal end of the syringe body.

11. The method of claim 8, wherein the pre-filled cartridge comprises a fluid medicament.

12. The method of claim 8, wherein the step of releasing the guard comprises releasing the guard from a retracted position to an extended position.

13. The method of claim 12, wherein the guard is retained in the retracted position by an adapter.

14. The method of claim 13, wherein the guard is operable to translate distally upon actuation of the distally projecting release.

15. The method of claim 14, wherein the guard is biased distally with a spring.

16. A method comprising the steps of:
inserting a pre-filled cartridge into a syringe body such that the pre-filled cartridge is axially aligned with the syringe body, the pre-filled cartridge comprising a cylindrical container having an inner surface operable to hold a fluid medicament therein, the pre-filled cartridge being operatively associated with the syringe body and further in communication with a needle connected to the syringe body, the pre-filled cartridge being operable to act as a plunger within the syringe body;

advancing the pre-filled cartridge distally within the syringe body;

establishing fluid communication between the pre-filled cartridge and the needle;

delivering a fluid medicament;

releasing a guard by depressing a distally projecting release with the inner surface of the cylindrical container, the distally projecting release having a free distal end and a fixed proximal end, the guard being in communication with the syringe body, to cover the needle; and locking the guard in a distally extended position such that the guard covers the needle.

17. The method of claim 16, wherein the distally projecting release is a passive release mechanism.

18. The method of claim 16, wherein the step of releasing a guard by depressing the distally projecting release comprises depressing the distally projecting release mechanism with the pre-filled cartridge.

19. The method of claim 16, wherein the pre-filled cartridge comprises a proximal fixed stopper and a distal moveable stopper.

20. The method of claim 19, wherein the distal moveable stopper is urged proximally to expel the fluid medicament from the pre-filled cartridge.

* * * * *